(12) United States Patent
Miller et al.

(10) Patent No.: US 7,439,414 B2
(45) Date of Patent: Oct. 21, 2008

(54) OXYGENATE CONVERSION CATALYST PROCESSING

(75) Inventors: Lawrence W. Miller, Palatine, IL (US); John J. Senetar, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 300 days.

(21) Appl. No.: 11/249,651

(22) Filed: Oct. 13, 2005

(65) Prior Publication Data

US 2007/0088187 A1    Apr. 19, 2007

(51) Int. Cl.
*C07C 1/00* (2006.01)
*B01J 38/72* (2006.01)

(52) U.S. Cl. .................... 585/640; 640/639; 502/21
(58) Field of Classification Search .............. 585/640, 585/921, 639; 502/21
See application file for complete search history.

(56) References Cited

U.S. PATENT DOCUMENTS 5,464,528 A * 11/1995 Owen et al. ................. 208/161

| | | | |
|---|---|---|---|
| 2003/0176753 A1 | 9/2003 | Levin et al. ................. | 585/640 |
| 2004/0059171 A1 | 3/2004 | Brookhart .................. | 585/638 |
| 2004/0064006 A1* | 4/2004 | Beech et al. ................ | 585/639 |
| 2004/0076554 A1 | 4/2004 | Kuechler et al. ............ | 422/139 |
| 2005/0027152 A1 | 2/2005 | Van Egmond et al. ....... | 585/639 |

OTHER PUBLICATIONS

"The Pall Gas Solid Separation System for the Chemical Process, Refining, and Mineral Industries: Advanced Metal Filters for Critical Gas Solid Separation Problems", Bulletin GSS-1a by Pall Corporation Fluid Processing Groups, East Hills, New York, 1987.

* cited by examiner

*Primary Examiner*—Glenn Caldarola
*Assistant Examiner*—In Suk Bullock
(74) *Attorney, Agent, or Firm*—James C Paschall

(57) ABSTRACT

Improved processing of spent catalyst from an oxygenate-containing feedstock to olefins conversion process is realized through the employment of a barrier filter to treat a catalyst particle-containing flue gas resulting from a catalyst regenerator. The barrier filter serves to separate the catalyst particles from the flue gas. Catalyst material so recovered can, with or without classifying, subsequently be appropriately recycled and further used.

11 Claims, 2 Drawing Sheets

OXYGENATE CONVERSION CATALYST PROCESSING

BACKGROUND OF THE INVENTION

This invention relates generally to conversion of oxygenates to olefins and, more particularly, to methods and apparatus for the processing of a catalyst employed in such an oxygenate conversion process.

DESCRIPTION OF THE RELATED ART

Light olefins serve as feed materials for the production of numerous chemicals. Light olefins have traditionally been produced through the processes of steam or catalytic cracking. The limited availability and high cost of petroleum sources, however, has resulted in a significant increase in the cost of producing light olefins from such petroleum sources.

The search for alternative materials for light olefin production has led to the use of oxygenates such as alcohols and, more particularly, to the use of methanol, ethanol, and higher alcohols or their derivatives. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins.

When a catalyst is exposed to oxygenates, such as methanol, to promote the reaction to olefins, carbonaceous material (coke) is generated and deposited on the catalyst. The accumulation of coke deposits on the catalyst interferes with the ability of the catalyst to promote the desired olefin production reaction and results in a spent catalyst. That is, as the amount of coke deposit increases, the catalyst typically loses activity and less of the feedstock is converted to the desired olefin product.

In view thereof, it is desirable to at least periodically regenerate the catalyst such as by removing the coke from the spent catalyst such as by combustion with oxygen, thus restoring the catalytic activity of the catalyst. The regenerated catalyst may then be exposed again to oxygenates to promote the desired conversion to olefins.

For example, spent catalyst can be continuously withdrawn from an oxygenate to olefins conversion reactor and regenerated in a regenerator, prior to return to the reactor. During such regeneration processing, the spent catalyst is commonly directed to the regenerator where combustion with oxygen-containing air burns coke deposits from the catalyst material.

A flue gas stream exits from the regenerator. Particulate emissions, such as largely composed of catalyst fines, can be a problem or concern with the processing of the flue gas from such a regenerator.

In addition, the catalysts commonly employed in the conversion of oxygenates to light olefins are typically of relative high value. Consequently, it is desirable to reduce or minimize the amount of such catalyst material that is lost or unrecovered, such as via entrainment in the flue gas.

Further, although rare, fluid catalytic processing may raise a concern relating to the potential or possibility of the loss of a large amount of catalyst from a vessel, such as the regenerator, due to a mechanical failure or a radical change in operating conditions.

Thus, there is a need and a demand for improvements in the processing of spent catalyst from an oxygenate-containing feedstock to olefins conversion process.

Furthermore, there is a need and a demand for improved methods for processing spent catalyst from an oxygenate-containing feedstock to olefins conversion process as well as an improved process and system for converting oxygenates to light olefins.

More particularly, there is a need and a demand for such improved methods, processes and systems that permit satisfaction of one or, preferably, more of the following conditions: more complete utilization of the oxygenate to olefin conversion catalyst; more complete particulate removal from the regenerator flue gas; incorporation and use of a regenerator cyclone of simplified design and or operation; and protection against large or massive catalyst lost such as in the event of a mechanical failure or a radical change in operating conditions.

SUMMARY OF THE INVENTION

A general object of the invention is to provide improved processing of spent catalyst from an oxygenate-containing feedstock to olefins conversion process.

A more specific objective of the invention is to overcome one or more of the problems described above.

The general object of the invention can be attained, at least in part, through a method of processing spent catalyst from an oxygenate-containing feedstock to olefins conversion process. In accordance with one preferred embodiment, such a method involves regenerating the spent catalyst to form a first regenerated catalyst portion and a flue gas containing catalyst particles. The flue gas containing catalyst particles is then treated with a barrier filter to separate catalyst particles from the flue gas.

The prior art generally fails to provide catalyzed conversion of oxygenate-containing feedstock to olefins that maximizes catalyst utilization and containment to as great as desired degree. Moreover, the prior art generally fails to provide as complete as desired removal of particulates from the flue gas of a catalyst regenerator in a catalyzed conversion of oxygenate-containing feedstock to olefins process and apparatus.

In accordance with another aspect of the invention, there is provided a process of converting oxygenates to light olefins. In accordance with one preferred embodiment, such a process includes charging a reactor with catalyst. An oxygenate-containing feed stream is fed to the reactor. The oxygenate-containing feed stream is contacted with the catalyst in the reactor and the oxygenate-containing feed stream is converted to the light olefins while spending the catalyst. At least a portion of the spent catalyst is regenerated, in a catalyst regenerator, to form a first regenerated catalyst portion and a flue gas containing catalyst particles. The first regenerated catalyst portion is returned to contact the oxygenate-containing feed stream. The flue gas containing catalyst particles is treated with a barrier filter to separate substantially all the catalyst particles from the flue gas. At least a portion of the catalyst particles separated from the flue gas are subsequently returned to the reactor. In accordance with one preferred embodiment, such return of the catalyst particles involves directly returning at least a portion of the catalyst particles separated from the flue gas to the catalyst regenerator with at least a portion of such returned catalyst particles in turn being returned to the reactor.

In accordance with another embodiment, there is provided a system for converting oxygenates to light olefins. The system includes a reactor for contacting an oxygenate-containing feed stream with catalyst and converting the oxygenate-containing feed stream to the light olefins. The system further includes a separator for separating spent catalyst from the light olefins. The system still further includes a regenerator for regenerating at least a portion of the spent catalyst to form a first regenerated catalyst portion and a flue gas containing catalyst particles. The system also includes a barrier filter to separate the catalyst particles from the flue gas.

Other objects and advantages will be apparent to those skilled in the art from the following detailed description taken in conjunction with the appended claims and drawings.

DETAILED DESCRIPTION OF THE INVENTION

Oxygenate-containing feedstock can be converted to light olefins in a catalytic reaction and the catalyst can be regenerated with the flue gas of the regenerator filtered to remove catalyst particles therefrom. In accordance with a preferred embodiment, at least a portion of the filtered catalyst particles are desirably ultimately returned to the reactor to contribute to further reaction processing.

More particularly, light oxygenates such as composed of one or more of methanol, ethanol, dimethyl ether, diethyl ether, or mixtures thereof, may react or otherwise be converted to light olefins such as ethylene or propylene in the presence of an appropriate selected catalyst in an exothermic reaction. Methanol and dimethyl ether are particularly preferred oxygenate feedstocks. The oxygenate-containing feedstock is introduced to the catalyst via a fluidized feed stream, which is preferably vaporized but may be liquid. The product or products obtained from the conversion process will depend on the feed stream, catalyst and conditions employed. Preferably products are hydrocarbons in the $C_2$ to $C_6$ carbon range. In one aspect, the desired product preferably contains light olefins having from about 2 to 4, more preferably from about 2 to 3 carbon atoms per molecule. For example, the methanol to olefin conversion process may be a vapor phase, fluid catalytic process that converts methanol to olefins, primarily ethylene and propylene.

Figure 1:
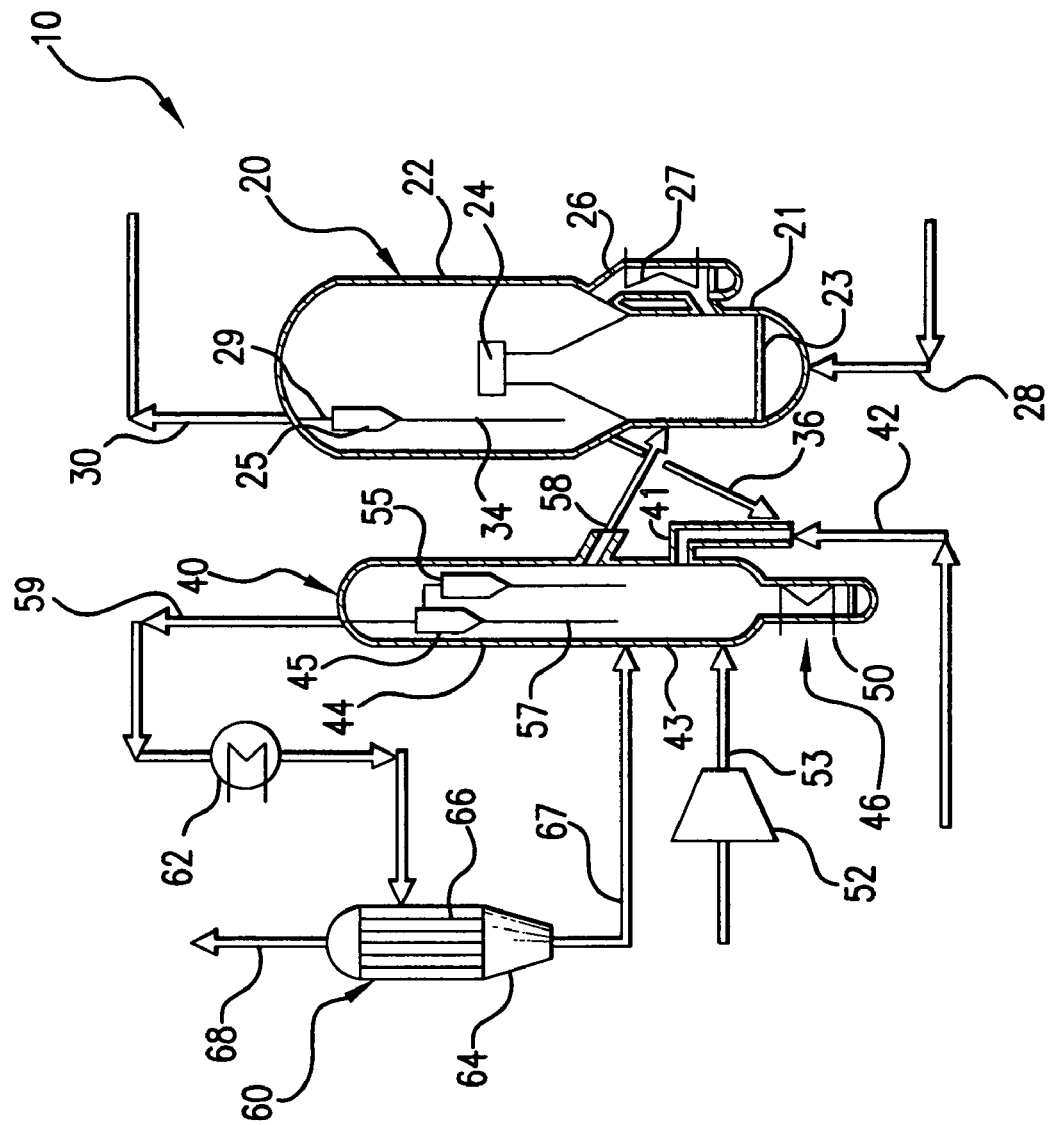
FIG. 1 is a simplified schematic diagram of a portion of a system for the conversion of an oxygenate-containing feedstock to olefins in accordance with one embodiment of the invention.

FIG. 1 schematically illustrates a system, generally designated by the reference numeral 10, for the conversion of an oxygenate-containing feedstock to olefins in accordance with one embodiment of the invention.

A feedstock comprising oxygenate, such as methanol, is contacted with a catalyst, such as containing a molecular sieve, in a reactor 20. As will be appreciated by those skilled in the art and guided by the teachings herein provided, such a feedstock may be commercial grade methanol, crude methanol or any combination thereof. Crude methanol may be an unrefined product from a methanol synthesis unit. Moreover, a feed comprising a methanol and water blend may have a methanol content of between about 65% and about 90% by weight. More preferably, a feed comprising methanol and water blend may have methanol in a range of between about 78% and about 82% by weight. In one preferred embodiment, a feed comprising a methanol and water blend may be about 80% methanol by weight.

A methanol to olefin unit designed to process about 2,500,000 metric tons per year of 95 wt-% methanol may have a feed rate of preferably between about 1500 and about 4000 kMTA and more preferably between about 2000 and about 3500 kMTA. The feed stream may comprise between about 0 and about 35 wt-% and more preferably between about 1 and about 25 wt-% water. The methanol in the feed stream may comprise between about 70 and about 100 wt-% and more preferably between about 75 and about 95 wt-% of the feed stream. The ethanol in the feed stream may comprise between about 0.01 and about 0.5 wt-% and more typically between about 0.1 and about 0.2 wt-% of the feed stream although higher concentrations may be beneficial. When methanol is the primary component in the feed stream, the higher alcohols in the feed stream may comprise between about 200 and about 2000 ppmw and more typically between about 500 and about 1500 ppmw. Additionally, when methanol is the primary component in the feed stream, dimethyl ether in the feed stream may comprise between about 10 and about 60 ppmw and more typically between about 20 and about 50 ppmw. Those skilled in the art and guided by the teachings herein provided will also appreciate that, if desired, high purity dimethyl ether can be used as feedstock for such an oxygenate-to-olefins conversion process.

Catalytic activity desirably should be maintained at a predetermined level for an oxygenate-containing feedstock to be continuously converted to olefins. Deposits on the catalyst that can impair catalytic activity should be removed without disrupting conditions for the reaction of oxygenate-containing feedstock to olefins. Fluidization of catalyst particles in or by various gaseous streams allows transport of the catalyst between the reactor 20, a catalyst regenerator 40 and a flue gas filter assembly 60, such as generally compose the system 10.

As shown in FIG. 1, the reactor 20 generally comprises a lower reactor section or chamber 21 and an upper reactor section 22, also sometimes referred to as a disengaging chamber. The lower reactor section 21, whereat the process reaction primarily occurs, has a feed distributor 23 to assist in distributing feedstock introduced thereinto through the conduit 28. The lower reaction section 21 also includes a fluidized bed of catalyst and an outlet riser 24. The upper reactor section 22 may constitute the primary vapor/catalyst separation zone. After the preliminary disengagement at the top of the outlet riser 24, the cyclones 25 (only one of which is shown to facilitate illustration and increase comprehension) carry the separation to a greater degree. Separated catalyst may be continually recycled from the upper reactor section 22 back down to the lower reactor section 21, such as via one or more recirculation conduits 26, to maintain the desired catalyst density in the lower reaction section 21. If desired, such catalyst being returned to the lower reaction section 21 can be first cooled, as signified by the element 27. Those skilled in the art and guided by the teachings herein provided will, however, appreciate that desired catalyst cooling can be appropriately conducted, in whole or in part, before, during or after passage through the recirculation conduit 26. Moreover, in embodiments comprising multiple recirculation lines, some or all of the recirculation lines may be without cooling. Thus, allowing control of the material density within the lower reaction section 21 independent of reactor cooling. Control valves (not shown) on the recirculation lines enable regulation of catalyst density in the lower reaction section 21.

The cyclones 25 separate catalyst from product vapors. Product vapors from each cyclone 25 are conveyed via a conduit 29 and ultimately to a product conduit 30 which directs the olefins and byproducts to a product recovery system.

Reaction conditions for the conversion of oxygenates to light olefins are known to those skilled in the art. Preferably, in accordance with the present invention, reaction conditions comprise a temperature between about 200° and about 700°

C., more preferably between about 300° and 600° C., and most preferably between about 400° and about 550° C., and a pressure between about 35 and about 414 kPa (gauge) (5 and 60 psig).

As will be appreciated by those skilled in the art and guided by the teachings herein provided, the reactions conditions are generally variable such as dependent on the desired products. For example, if increased ethylene production is desired, then operation at a reactor temperature between about 475° and about 550° C. and more preferably between about 500° and about 520° C., may be preferred. Further, for ethylene production, operating pressures in the range of about 35 to about 138 kPa (gauge) (5 to 20 psig) may be preferred.

If increased propylene production is desired, then operation at a reactor temperature between about 350° and about 475° C. and more preferably between about 400° and about 430° C. may be preferred. Further, propylene production can desirably be favored by operation at a pressure of between about 35 and about 276 kPa (gauge) (5 and 40 psig).

The light olefins produced can have a ratio of ethylene to propylene of between about 0.5 and about 2.0 and preferably between about 0.75 and about 1.25. If a higher ratio of ethylene to propylene is desired, then the reaction temperature is higher than if a lower ratio of ethylene to propylene is desired. The preferred feed temperature range is between about 120° and about 200° C. More preferably the feed temperature range is between about 180° and 200° C.

Catalyst separated in the cyclones 25 drop through the diplegs 34 into the bottom of the disengaging chamber 22. Valves (not shown) or the like at the bottom of the cyclones 25 prevent backflow of catalyst up the cyclone diplegs 34.

A portion of the spent catalyst settling into the bottom of the disengaging chamber 22 is directed into the recirculation conduit 26. Another portion of the spent catalyst in the bottom of the disengaging chamber 22 is directed to the catalyst regenerator 40 through a conduit 36. More particularly, spent catalyst is transferred from the reactor 20 to the regenerator 40 via an exposed catalyst standpipe 41 with lift air from a distributor 42.

As will be appreciated by those skilled in the art and guided by the teachings herein provided, prior to the spent catalyst being regenerated, hydrocarbons may be desirably stripped or otherwise effectively removed from the spent catalyst such as by means of a stripper (not shown) such as employing steam or other effective stripping medium.

As identified above, during the conversion of oxygenates to light olefins, a carbonaceous material, i.e., coke, can deposit on the catalyst. Such coke deposit material can have the effect of reducing the number of active sites on the catalyst which thereby affects the extent of the conversion. The catalyst becomes spent as coke deposits accumulate on the catalyst and decreases the ability of the catalyst to assist in the conversion of the oxygenate-containing feedstock to olefins. Thus, during the fluidized bed conversion process, a portion of the spent or coked catalyst is withdrawn from the reactor and regenerated in a regenerator to remove at least a portion of the coke. Preferably, the coke is removed from the catalyst by oxidative regeneration in regenerator. After the catalyst is regenerated to remove coke deposit material, and thereby increase the amount of active catalyst sites, the regenerated catalyst returns to the reactor and further contacts the feed stream in order to convert oxygenates to light olefins. The system is operated such that a sufficient quantity of active catalyst sites are provided within the fluidized reaction chamber in order to enhance the conversion of the feed stream to the desired product without enhancing the conversion to undesired by-products.

In one embodiment, the regenerator 40 comprises a fluid bed section 43, an upper disengaging section 44 comprising cyclones 45, a lower section 46 comprising regenerator catalyst coolers 50. A blower 52 on the line 53 supplies combustion gas to the regenerator 40. Combustion gas used in the practice of the invention may contain oxygen ($O_2$) or other oxidants. It may be preferred to supply oxygen in the form of air. The air or other combustion gas, if desired, can be diluted with nitrogen, $CO_2$, flue gas, or steam, for example, or alternatively enriched with oxygen.

In operation, the regenerator 40 contacts spent catalyst with combustion gas such that contact with oxygen combusts coke from the catalyst as it passes upwardly through fluid bed section 43. A small portion of the catalyst remains entrained with the combustion gases and enters the inlet 55 of the cyclones 45 which separate much of the entrained catalyst from the combustion gases. The cyclones 45 serve to convey such separated catalyst to the regenerator lower section 46 via the diplegs 57.

At least a portion of the regenerated catalyst particles may be cooled by the coolers 50 such as located at the bottom of the regenerator 40. The coolers 50 may cool by means of vaporizing water into steam. Heat exchange tubes are bayonet style tubes having an outer tube that contacts the catalyst and an inner tube for circulating a cooling fluid.

A portion of the regenerated catalyst may be recirculated to the lower reaction chamber 21 through one or more recycle conduits 58. Flow through the recycle conduits 58 may be regulated by a control valve (not shown).

The combustion process occurring in the regenerator 40 produces or results in a flue gas. Combustion flue gases are discharged from the regenerator 40 via the conduit 59. In one embodiment, typical flue gas for a regenerator, such the regenerator 40, may comprise: 2-11% $H_2O$, 3-7% $O_2$, 75-80% $N_2$, and 10-15% $CO_2$, on a volume percent basis. In addition, there may be residual CO in the flue gas of the regenerator 40.

As identified above, particulate emissions, such as largely composed of catalyst particles, particularly catalyst particles in the form of catalyst fines, can be a problem or concern with the processing of the flue gas from such a regenerator. As shown in FIG. 1, the system 10 includes a flue gas filter assembly 60 such as desirably disposed downstream of the separation of products vapors (e.g., light olefins) from catalyst particles and the separator or separators associated with such separation. More particularly, the flue gas, such after passage through a cooler 62, is introduced into the flue gas filter assembly 60.

The flue gas filter assembly 60 includes a filter housing 64 or the like and one or more filtration elements 66 housed or otherwise appropriately contained therewithin. In a preferred embodiment, a barrier filter comprising a sintered metal filtration element constitutes a preferred form of filtration element.

Catalyst fines, separated from the flue gas through or by treatment with the filtration elements 66, can desirably be returned to the regenerator 40 as shown or represented by the conduit or stream 67. As shown, such return of these catalyst particles is desirably to a regenerator location such that they are preferentially ultimately returned to the reactor.

The flue gas, now free of the separated catalyst particles, can be passed through a conduit 68 for further treatment or otherwise appropriately disposed. In accordance with certain preferred embodiments, the filter is desirably self-cleaning during normal operation. Therefore, it is possible for such a system to incorporate only a single filter assembly.

As will be appreciated by those skilled in the art and guided by the teachings herein provided, systems for the conversion of an oxygenate-containing feedstock to olefins can, if desired, include two or more such or similar flue gas filter assemblies, such as in parallel placement and operation, such as to provide additional processing flexibility such as by permitting continued operation while allowing the performance of needed or desired maintenance to another of such filter assemblies.

Moreover, the process inclusion of a barrier filter as described above, can desirably provide protection in the event of the loss of a large amount of catalyst from the regenerator, such as due to a mechanical failure or a radical change in operating conditions. In particular, upon the occurrence of such an event, the barrier filter can serve to contain the catalyst and thus prevent catalyst release to the atmosphere.

Figure 2:
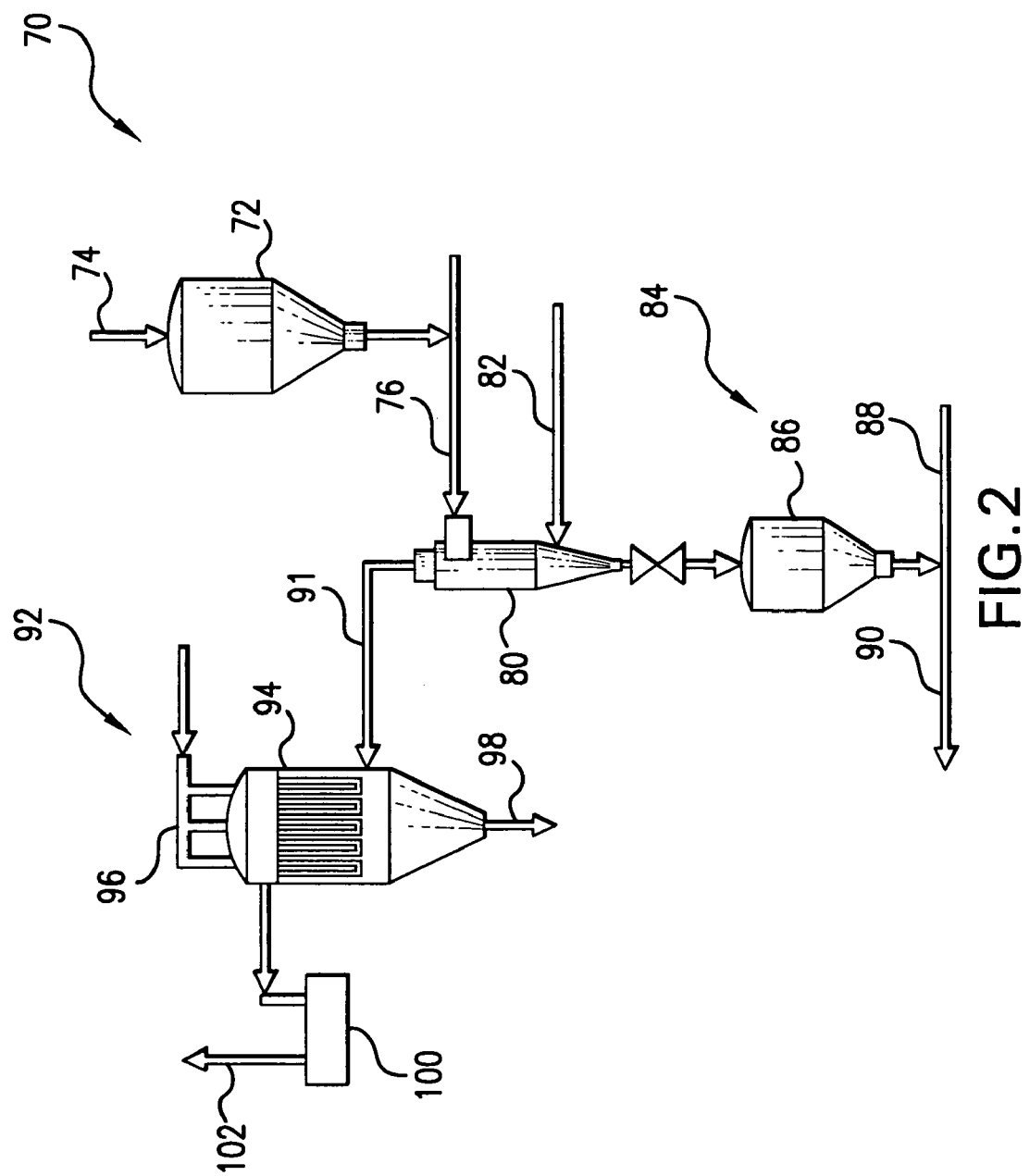
FIG. 2 is a simplified schematic diagram of a flue gas fines classifier system in accordance with one embodiment of the invention.

FIG. 2 is a simplified schematic diagram of a flue gas fines classifier system 70 in accordance with one embodiment and whereby catalyst particles recovered or removed, as described above, via a filtration element and such as represented by the stream 67 shown in FIG. 1 and described above, can be desirably and appropriately processed between the filtration assembly 60 and the regenerator 40.

The flue gas fines classifier system 70 includes a fines surge hopper 72 into which catalyst fines, such as recovered or removed from the regenerator flue gas, as described above via one or more filtration elements, are fed or introduced such as shown by the feed line 74. The fines surge hopper 72 serves as a collection vessel capable of holding catalyst collected from the flue gas filters over a desired period of time. In one embodiment, the system incorporates a fines surge hopper having a holding capacity for approximately one week's worth of catalyst fines. As will be appreciated, dry air can be used such as in the form of a continuous purge so as to purge the surge hopper of flue gas and moisture to keep the catalyst dry.

The catalyst fines from the fines surge hopper 72 can then be appropriately conveyed such as by means of dry air supplied through the conduit 76 to a fines classifier 80. To assist in effecting the desired classification, reverse flow air can also be supplied to the classifier 80 such as via the conduit 82.

In one embodiment, the classifier is desirably capable of separating material of about 10 to about 30 microns or less from the balance of the catalyst material. In certain embodiments, it is desirable to separate material with a particle size of less than 20 micron.

Those skilled in the art and guided by the teachings herein provided will appreciate that classifiers of various design are available and can be used to effect desired classification of the fines and thus the it is to be understood that the broader practice of the invention is not limited by or to the use of specifically designed classifiers. In accordance with one embodiment, a classifier that cyclonically processes catalyst fines is preferred. Examples of such classifiers include aerodynamic particle classifiers available from Fisher-Klosterman, Inc. of Louisville, Ky. and classifiers available from the Buell Division of Fisher-Klosterman, Inc., Lebanon, Pa.

Coarser or larger size material, such as material larger than the 10 to 30 microns in the above example, or, in certain embodiments 20 microns or larger can then be appropriately conveyed via a return system 84 such as composed of the hopper 86 and by means of lift air such as supplied via a conduit 88, through a conduit 90 back to the regenerator (item 40 in FIG. 1). Those skilled in the art and guided by the teachings herein provided will appreciate that such recovery and recycle of catalyst material can desirably extend the overall life of the catalyst material employed in the process.

Finer size material, such as material of about 10 to 30 microns or less, or, in certain embodiments less than 20 microns, can then be appropriately conveyed such as via a conduit 91 to a disposal system 92 such as composed of a bag house 94 wherein barrier filters such as in the form of fabric bag filters, filter the catalyst particles contained within the stream passing therethrough. Backflush air, such as provided by the conduits 96, can be employed such as to effect removal of such catalyst particles from the fabric bag, to form a fines conduit 98 for ultimate disposal. A blower 100 can be employed to exhaust the treated flue gas to the atmosphere, as shown by the conduit 102.

The filter and classifier and the operation thereof can be appropriately adjusted to accommodate various changes in process conditions. For example, in the event the regenerator cyclones develop a hole or wear with age such that the regenerator cyclones permit or allow an increased relative amount of solids to pass with the flue gas, the filter and the classifier provide sufficient processing flexibility to accommodate such increased solids loadings and to permit the recycle of recovered solids. In particular, valuable larger particles, such as may have been included with the flue gas as a result of such regenerator cyclone operation, can be recovered and appropriately recycled.

Moreover, those skilled in the art and guided by the teachings herein provided will further appreciate that the size of the fines recovered or alternatively the size of the fines discarded can be appropriately adjusted to meet the needs of a particular application.

The system and processing inclusion of a barrier filter as described above, may appropriately allow for the regenerator cyclones to be designed to operate at a lower efficiency. In addition, further capital costs can be saved through simplification of the cyclone design and/or decreasing the number of stages.

Thus, such filter and classifier use provides a relatively inexpensive processing scheme that provides sufficient processing flexibility to accommodate changes in process conditions.

Embodiments, such as described above, desirably provide or result in improved catalyst utilization in the catalyzed conversion of oxygenate-containing feedstock to olefins. Those skilled in the art and guided by the teachings herein provided will further appreciate that the rate of deactivation of typical or common olefin-to-oxygenate catalysts can be relatively low as compared to catalysts employed in other common processing schemes, such as catalyst materials employed in fluid catalytic cracking (FCC) processing. Through the practice of embodiments such as described above, the loss of valuable olefin-to-oxygenate catalyst can desirably be minimized, such as through the above-described utilization of classification processing and return of catalyst particles. Moreover, such embodiments can desirably provide or result in improved containment of catalyst used in the catalyzed conversion of oxygenate-containing feedstock to olefins. Such embodiments can also desirably provide more complete removal of particulates from the flue gas of a catalyst regenerator in a catalyzed conversion of oxygenate-containing feedstock to olefins process and apparatus.

While the invention has been described above making reference to the inclusion of a classifier or the like, those skilled in the art and guided by the teachings herein provided will appreciate that the broader practice of the invention is not necessarily so limited. For example, if desired, all or virtually all of the fines can be recycled to the process, e.g., to the reactor, such as by-passing the classifier with all or portions of the recovered solids.

Moreover, while embodiments have been described above making specific reference to return of catalyst particles, e.g., catalyst fines, to the reactor involving directly returning at least a portion of the catalyst particles separated from the flue gas to the catalyst regenerator with at least a portion of such returned catalyst particles in turn being returned to the reactor, it is to be understood that the broader practice of the invention is not necessarily so limited. For example, if desired, direct return of catalyst particles to the reactor can be achieved such as with the use of an inert gas for classifying and transport of the catalyst particles to the reactor.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A process of converting oxygenates to light olefins comprising:
    charging a reactor with catalyst;
    feeding an oxygenate-containing feed stream to the reactor;
    contacting the oxygenate-containing feed stream with the catalyst in the reactor and converting the oxygenate-containing feed stream to the light olefins while spending the catalyst;
    regenerating at least a portion of the spent catalyst in a regenerator to form a first regenerated catalyst portion and a flue gas containing catalyst particles;
    returning the first regenerated catalyst portion to contact the oxygenate-containing feed stream;
    treating the flue gas containing catalyst particles with a barrier filter to separate substantially all the catalyst particles from the flue gas; and
    returning at least a portion of the catalyst particles separated from the flue gas to the reactor.

2. The process of claim 1 wherein said returning at least a portion of the catalyst particles separated from the flue gas to the reactor comprises:
    directly returning at least a portion of the catalyst particles separated from the flue gas to the regenerator; and
    returning at least a portion of such returned catalyst particles from the regenerator to the reactor.

3. The process of claim 1 wherein said catalyst regeneration is continuous.

4. The process of claim 1 additionally comprising classifying the separated catalyst particles.

5. The process of claim 4 wherein said returning of at least a portion of the catalyst particles separated from the flue gas to the reactor comprises returning the separated catalyst particles classified as at least 10 to 30 microns to the reactor.

6. The process of claim 4 additionally comprising discarding the separated catalyst particles classified as less than 10 to 30 microns.

7. The process of claim 3 wherein said classifying of the separated catalyst particles comprises cyclonic processing of the separated catalyst particles.

8. The method of claim 1 wherein the separated catalyst particles are classified into at least two size fractions including a first fraction of smaller sized catalyst fines and a second fraction of larger sized catalyst fines and wherein said method additionally comprises:
    returning the second classified fraction of catalyst fines to the reactor; and
    discarding the first classified fraction of catalyst fines.

9. The method of claim 8 wherein the second classified fraction of catalyst fines consists essentially of particles having a size of at least 10 to 30 microns.

10. The method of claim 8 wherein the first classified fraction of catalyst fines consists essentially of particles having a size of no more than 10 to 30 microns.

11. The method of claim 1 wherein said treating of the flue gas containing catalyst particles with a barrier filter comprises treating the flue gas containing catalyst particles with a sintered metal barrier filter.

* * * * *